US011881017B2

(12) United States Patent
Pham et al.

(10) Patent No.: US 11,881,017 B2
(45) Date of Patent: Jan. 23, 2024

(54) TURBIDITY DETERMINATION USING MACHINE LEARNING

(71) Applicant: X Development LLC, Mountain View, CA (US)

(72) Inventors: Harrison Pham, Sunnyvale, CA (US); Kathy Sun, Boulder Creek, CA (US); Alex Ryan Edwards, Palo Alto, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 17/703,746

(22) Filed: Mar. 24, 2022

(65) Prior Publication Data

US 2023/0306734 A1 Sep. 28, 2023

(51) Int. Cl.
G06V 20/05 (2022.01)
G06T 7/50 (2017.01)
H04N 23/60 (2023.01)
G06V 20/60 (2022.01)
G01N 33/18 (2006.01)
G06V 10/774 (2022.01)
H04N 23/56 (2023.01)
H04N 23/695 (2023.01)

(52) U.S. Cl.
CPC ............ G06V 20/05 (2022.01); G01N 33/18 (2013.01); G06T 7/50 (2017.01); G06V 10/7747 (2022.01); G06V 20/60 (2022.01); H04N 23/56 (2023.01); H04N 23/695 (2023.01); *G06T 2207/20081* (2013.01)

(58) Field of Classification Search
CPC .... G06V 20/05; G06V 10/7747; G06V 20/60; G06T 7/50; G06T 2207/20081; H04N 23/695; H04N 23/56; G01N 33/18
See application file for complete search history.

(56) References Cited

U.S. PATENT DOCUMENTS

| 7,710,465 B2 | 5/2010 | Takita | |
| 2020/0107524 A1* | 4/2020 | Messana | A01K 61/10 |
| 2020/0223719 A1 | 7/2020 | Piironen et al. | |
| 2021/0041368 A1* | 2/2021 | Lu | G01N 21/78 |

(Continued)

FOREIGN PATENT DOCUMENTS

JP H0283004 3/1990

OTHER PUBLICATIONS

Markussen "Parchar—Characterization of Suspended Particles Through Image Processing in Matlab", Article in Journal of Open Research Software, Jul. 2016.*

(Continued)

*Primary Examiner* — James T Boylan
(74) *Attorney, Agent, or Firm* — Fish & Richardson P.C.

(57) ABSTRACT

Methods, systems, and apparatus, including computer programs encoded on a computer storage medium, for determining turbidity of water using machine learning. One of the methods includes obtaining, by a camera, an image of water; detecting, using a blob detector, a plurality of blobs in the image that represent particles suspended in the water; determining a distribution of the plurality of blobs; determining, from the distribution of the plurality of blobs, a measurement associated with turbidity of the water; and providing a signal associated with the measurement.

23 Claims, 3 Drawing Sheets

(56) References Cited

U.S. PATENT DOCUMENTS

| | | | |
|---|---|---|---|
| 2021/0085165 A1* | 3/2021 | Rauniyar | A61B 1/000094 |
| 2021/0329892 A1* | 10/2021 | Kozachenok | A01K 61/95 |
| 2022/0237799 A1* | 7/2022 | Price | G06T 7/11 |
| 2022/0400657 A1* | 12/2022 | Humphreys | A23K 50/80 |

OTHER PUBLICATIONS

Girshick, "Fast r-cnn," Proceedings of the IEEE international conference on computer vision, 2015, pp. 1440-1448.

Karnawat et al., "Turbidity detection using Image Processing," International Conference on Computing, Communication and Automation, 2016, pp. 1086-1089.

Liu et al., "A Review of Turbidity Detection Based on Computer Vision," IEEE, 2010, 6:60586-60604.

Liu et al., "SSD: Single shot multibox detector," Computer Vision—ECCV 2016, European Conference on Computer Vision, Sep. 2016, 9905:21-27.

Redmon et al., "You only look once: Unified, real-time object detection," Proceedings of the IEEE Conference on Computer Vision and Pattern Recognition, 2016, pp. 779-788.

Ren et al., "Faster r-cnn: Towards real-time object detection with region proposal networks," Advances in neural information processing systems, 2015, 28:91-99.

Akshaya et al., "Sparse representation to localize objects in underwater acoustic images," IEEE International Conference on Electrical, Computer and Communication Technologies (ICECCT), Mar. 5-7, 2015, pp. 1-5.

International Search Report and Written Opinion in International Appln. No. PCT/US2023/015857, dated Jun. 16, 2023, 21 pages.

Yao et al., "Effect of particle size distribution on turbidity under various water quality levels during flocculation processes," Desalination, Oct. 8, 2014, 354:116-124.

* cited by examiner

TURBIDITY DETERMINATION USING MACHINE LEARNING

TECHNICAL FIELD

This disclosure application relates generally to determining turbidity in an aquaculture environment.

BACKGROUND

Turbidity is the measurement of relative clarity of a liquid. It is an optical characteristic of water and is a measurement of the amount of light that is scattered by material in the water when a light is shined through the water. Turbidity detection systems use devices to measure turbidity of water. For example, a nephelometer can be used by a human operator to determine the turbidity of water.

Turbidity in aquaculture environments influence both the behavior of aquatic livestock and the management of the environment. For example, some livestock feed better when they can visually perceive food, so the level of illumination and the clarity of the environment influence their feeding behavior, and consequently, systems that control feeding within the environment. In addition, illumination and imaging devices can be integral parts of livestock management, and turbidity of the water can influence the operation of such devices. For example, imaging devices can be used to measure the health of members of a livestock population, for example, by detecting parasitic infestations, but such devices can require proper levels of illumination.

However, existing approaches to measuring turbidity of water have drawbacks. For example, turbidity detection systems usually require manual involvement, which is not possible in an environment that is largely automated. Turbidity detection technologies such as nephelometers can require the introduction and maintenance of additional devices.

SUMMARY

In general, innovative aspects of the subject matter described in this specification relate to determining turbidity in an aquaculture environment. A framework may be implemented as computer programs on one or more computers in one or more locations that uses perception data, produced by applying computer vision and machine learning techniques and configured for consumption by one environmental management system, to determine turbidity of an aquaculture environment. Computer vision and image processing techniques such as blob detectors can be used to detect particles suspended in the water that causes turbidity. A turbidity prediction engine that includes a machine learning model can be trained to automatically determine a measurement associated with the turbidity of the water. Such additional determinations can be made without introducing additional devices into the environment, and can be used to improve the management of the environment.

One innovative aspect of the subject matter described in this specification is embodied in a method that includes obtaining, by a camera, an image of water; detecting, using a blob detector, a plurality of blobs in the image that represent particles suspended in the water; determining a distribution of the plurality of blobs; determining, from the distribution of the plurality of blobs, a measurement associated with turbidity of the water; and providing a signal associated with the measurement.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some aspects, the measurement associated with the turbidity of the water represents Nephelometric Turbidity Units (NTU). In some implementations, providing the signal associated with the measurement includes: obtaining first criteria associated with the measurement; determining that the measurement satisfies the first criteria; and in response, changing a setting of lights. In some implementations, providing the signal associated with the measurement includes: obtaining second criteria associated with the measurement; determining that the measurement satisfies the second criteria; and in response, changing a position of the camera.

In some implementations, determining the distribution of the plurality of blobs includes: determining sizes of the plurality of blobs; and generating a histogram of the sizes of the plurality of blobs. In some implementations, determining, from the distribution of the plurality of blobs, the measurement associated with the turbidity of the water includes: providing the histogram of the sizes of the plurality of blobs as an input to a machine learning model; and generating the measurement associated with the turbidity of the water using the machine learning model. In some aspects, the machine learning model is trained with training data including images previously captured by the camera and respective ground truth measurement measured by a turbidity sensor.

In some implementations, determining the distribution of the plurality of blobs includes: detecting a particular object in the image using an object detector; determining that a subset of the plurality of blobs detected in the image overlaps with the particular object; and determining the distribution of the plurality of blobs to not represent the subset of the plurality of blobs. In some implementations, providing the signal associated with the measurement includes providing the signal that triggers a change of a setting of the camera. In some implementations, providing the signal associated with the measurement includes: obtaining third criteria associated with the measurement; determining that the measurement satisfies the third criteria; and in response, changing a setting of a feeding subsystem.

Particular embodiments of the subject matter described in this specification can be implemented so as to realize one or more of the following advantages. The techniques described below can be used to determine turbidity of an aquaculture environment, by reusing data produced for an environmental system, thereby eliminating the need to introduce additional equipment to the environment. The measurement associated with the turbidity of the water can be provided to the environmental system and the environmental system can adjust the setting of the illumination and the imaging devices based on the measurement of the turbidity of the water.

The details of one or more implementations of the subject matter of this specification are set forth in the accompanying drawings and the description below. Other features, aspects,

BRIEF DESCRIPTION OF THE DRAWINGS

Like reference numbers and designations in the various drawings indicate like elements.

DETAILED DESCRIPTION

Aquaculture includes the farming of marine or freshwater organisms such as fish, crustaceans and mollusks. Aquaculture is important to the health of marine or freshwater ecosystems, which can suffer from overharvesting. Experience indicates over half of all fish and shellfish come from aquaculture, and in the absence of aquaculture, substantial, and perhaps irreversible, strain on marine ecosystems could result.

Some aquaculture environments use various sensors to aid in the care and feeding of the aquatic livestock. Sensors can provide measurements that are used to monitor environmental conditions such as light and temperature. The measurements can also be used when producing information such as estimates of the population of livestock, determinations of parasite infestations, and so on. Sensors can be attached in fixed positions, or attached to one or more rigs that patrol the environment.

Optical properties, particularly turbidity, can vary within an aquaculture environment for a variety of reasons. For example, turbidity can increase when foul weather causes floor sediment to circulate or when livestock detritus accumulates.

Changes in turbidity are relevant to effective management of an aquaculture environment. For example, fish typically feed more efficiently when they can visually perceive the food pellets, and turbidity reduces their ability to see the pellets. In more turbid conditions, a rig containing sensors might be instructed to seek clearer water, allowing the sensors to work more effectively. Increases in turbidity can reduce the effectiveness of illumination devices, potentially requiring increases or decreases in illumination strength to enable proper imaging. Increases in turbidity can correlate with foul weather, and upon detecting turbidity, an alert can be raised to assist farmers.

However, introducing additional sensors to the environment can increase the complexity of managing the environment. Sensors can fail or become fouled in harsh aquatic environments, increasing the frequency of needed repairs, which can require a technician both to locate the faulty component and to replace or repair it. Further, additional equipment can produce electrical signals that increase the electrical noise in the environment, which can affect the operation of delicate electronics in the environment.

Figure 1:
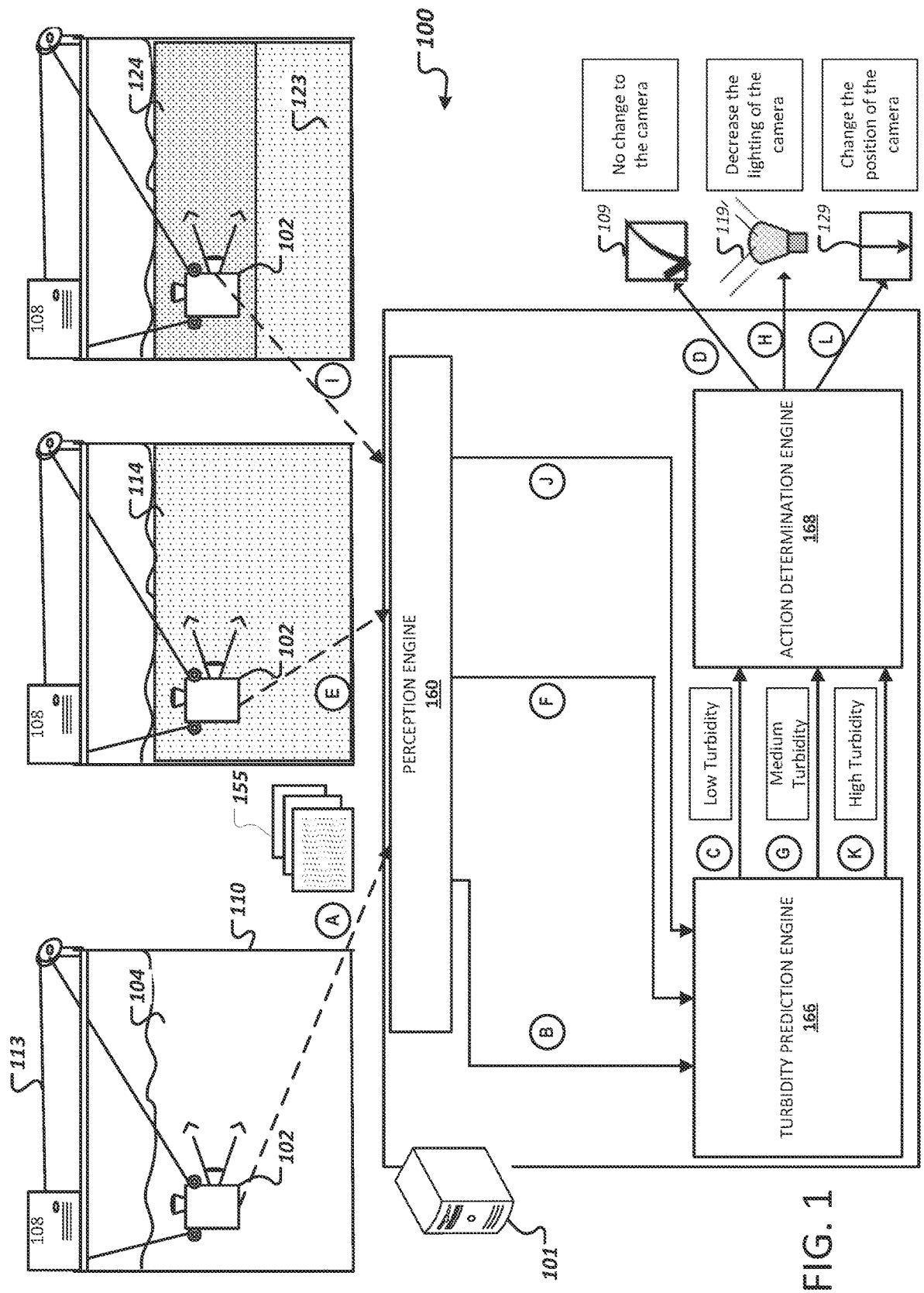
FIG. 1 is a diagram illustrating an example system for determining turbidity in an aquaculture environment.

FIG. 1 is a diagram illustrating an example system 100 for determining turbidity in an aquaculture environment. More specifically, the system 100 detects, from an image of water, a plurality of blobs that represent particles suspended in the water and determines turbidity of the water from the distribution of the plurality of the blobs.

The system 100 can include an enclosure 110 with a winch subsystem 108 and one or more camera subsystems 102 each containing one or more cameras, including stereo cameras. The system 100 can include a perception engine 160, a turbidity prediction engine 166, and an action determination engine 168. The perception engine 160, the turbidity prediction engine 166, and the action determination engine 168 can be implemented in one or more computing devices 101 (e.g., computers or servers). The one or more computing devices 101 can be at a location that is away from the water 104 and the one or more camera subsystems 102, and can communicate with the one or more camera subsystems 102 through a wired or wireless network. In some implementations, the one or more computing devices 101 can be a part of the one or more camera subsystems 102.

The enclosure 110 may or may not enclose livestock that can be aquatic creatures, which swim freely within the confines of the enclosure 110. In some implementations, the aquatic livestock stored within the enclosure 110 can include fish, crustaceans, mollusks, or other aquatic lifeforms. The livestock can include, for example, juvenile fish, koi fish, sharks, salmon, bass, and shrimp.

In addition to the aquatic livestock, the enclosure 110 contains water 104, e.g., seawater, freshwater, or rainwater, although the enclosure can contain any fluid that is capable of sustaining a habitable environment for the aquatic livestock. Particles in the water can cause turbidity of the water. Material that causes water to be turbid include clay, silt, very tiny inorganic and organic matter, algae, dissolved colored organic compounds, plankton, and other microscopic organisms. For example, marine snow (i.e., a shower of organic material falling from upper waters to the deep ocean) can cause high turbidity in the water. The water 104 can have low turbidity because there are less particles suspended in the water. Low turbidity can indicate that the water 104 is clear. The water 114 can have medium turbidity, indicating that the water has medium clarity. The first region 124 of water can have high turbidity because there are dense particles suspended in the water, indicating that the water has very poor visibility.

In some implementations, the system 100 may be anchored to a structure such as a pier, dock, or buoy. For example, instead of being confined within the enclosure 110, the livestock can be free to roam a body of water, and the system 100 can monitor livestock within a certain area of the body of water without the enclosure 110.

The winch subsystem 108 may move the camera subsystem 102 in a patrol pattern, e.g., up and down to different depths in the enclosure 110. For example, the camera subsystem 102 may patrol up and down within the enclosure 110 while it monitors fish feeding. The winch subsystem 108 can include one or more motors, one or more power supplies, and one or more pulleys to which the cord 113, which suspends the camera subsystem 102, is attached. A pulley is a machine used to support movement and direction of a cord, such as cord 113. Although the winch subsystem 108 includes a single cord 113, any configuration of one or more cords and one or more pulleys that allows the camera subsystem 102 to move and rotate, as described herein, can be used.

The winch subsystem 108 may activate one or more motors to move the cord 113. The cord 113, and the attached camera subsystem 102, can be moved along the x, y, and z-directions, to a position corresponding to the instruction. A motor of the winch subsystem 108 can be used to rotate the camera subsystem 102 to adjust the horizontal angle and the vertical angle of the sensor subsystem. A power supply can power the individual components of the winch subsystem. The power supply can provide AC and DC power to each of the components at varying voltage and current levels. In some implementations, the winch subsystem can include multiple winches or multiple motors to allow motion in the x, y, and z-directions.

Each camera subsystem 102 can include one or more image capture devices that can point in various directions, such as up, down, to any side, or at other angles. Each camera subsystem 102 can take images using any of its included imaging devices, and an enclosure 110 can contain multiple camera subsystems 102. A camera subsystem 102 can provide image data 155, which can be individual image data or video image data, represented in any appropriate format. For individual images, formats can include JPEG, TIFF, BMP, raw, etc. For video image data, formats can include MP4, MOV, WAV, AVI, etc. The image data 155 can be provided to a perception engine 160.

The perception engine 160 can receive the image data 155 and apply computer vision models such as image classification, object detection, object tracking, etc., to produce perception data of a scene captured by the image data 155. The particles suspended in the water can reflect light and can be captured as white dots or blobs in the image data 155. The perception engine 160 can apply a blob detector to detect a plurality of blobs in the image data 155 and the plurality of blobs can represent particles suspended in the water. The blob detector is a computer vision algorithm that detects a continuous area that is enclosed and has a certain brightness level and a certain size compared to surrounding regions. Examples of blob detectors include Laplacian of Gaussian (LOG), Difference of Gaussian (DOG), Determinant of Hessian (DOH), Connected Components, and so on.

The perception engine 160 can generate a distribution of the plurality of blobs. For example, the perception engine 160 can determine the sizes of the plurality of blobs and can generate a histogram of the sizes of the plurality of blobs. The histogram can include a plurality of size intervals and can include a count of the detected blobs in each size interval. The perception engine 160 can provide the distribution of the blobs (e.g., the histogram of the sizes of the blobs) to a turbidity prediction engine 166.

The turbidity prediction engine 166 can determine, from the distribution of the plurality of blobs, a measurement associated with the turbidity of the water. The distribution of the blob can indicate turbidity of the water. For example, a large number of small particles (e.g., a size that is smaller than 0.5 mm) in the water can result in a large number of small size blobs, indicating high turbidity of the water. The measurement associated with the turbidity of the water can be in Nephelometric Turbidity Units (NTU).

In some implementations, the turbidity prediction engine 166 can provide the histogram of the sizes of the plurality of blobs as an input to a machine learning model and can generate the measurement associated with the turbidity using the machine learning model. The machine learning model can be any type of model that can generate a prediction score from a sequence of input data, such as a regression model. The machine learning model can be trained with training data (e.g., a distribution of blobs in an image previously captured by one or more cameras) and respective ground truth measured by a turbidity sensor. In some implementations, the turbidity prediction engine 166 can use a rule based model to generate the measurement associated with the turbidity of the water. The rule based model can be determined based on previous observations and experiences of the relationship between the distribution of the blobs and the turbidity of the water.

The turbidity prediction engine 166 can provide a signal associated with the measurement of the turbidity of the water (e.g., providing the signal that triggers a change of a setting of the camera subsystem 102). In some implementations, the turbidity prediction engine 166 can provide the measurement associated with the turbidity of the water to an action determination engine 168. The action determination engine 168 can determine an action based on the measurement associated with the turbidity of the water.

Recommended actions can relate to various aspects of aquaculture management. For example, when turbidity is determined to be extremely high, indicating that the camera might be rendered inoperable, the recommended action might indicate that the images produced should not be processed, reducing the computational load. In addition, the recommended action might indicate that the rig should patrol at different depths in search of clearer water. In another example, in moderate turbidity, the recommended action might indicate that illuminations devices should produce stronger lighting to compensate for the reduced clarity. Such an action can enable parasite detection to operate effectively despite suboptimal environmental conditions. Similarly, in response to detecting increased turbidity, since fish can eat less aggressively when they cannot see the feed, the recommended action can indicate that the feeding subsystem should reduce the quantity of feed released or the rate at which it is released. In still another example, if the turbidity is high, an indicator can be associated with the data produced by various subsystems, including the biomass estimation subsystem and the parasite detection subsystem reflecting lower confidence in the data. In yet another example, in high turbidity, the perception system itself might operate sub-optimally, incorrectly determining that multiple perceptions of the same fish are different fish.

Recommended actions can also be produced in response to changes and to rates of change in turbidity. For example, in response to sustained turbidity over a period of time, a recommended action can indicate that the biomass estimation subsystem should increase the number of measurement days to compensate for lower visibility. In another example, if turbidity is high, but turbidity is trending lower, the recommended action can indicate that the feeder subsystem should delay feeding for some period.

In some implementations, the action determination engine 168 can obtain first criteria associated with the measurement of the turbidity, and can determine that the measurement satisfies the first criteria. In response to determining that the measurement satisfies the first criteria, the action determination engine 168 can change a setting of lights. In response to determining that the measurement does not satisfy the first criteria (e.g., the water is clear because of low turbidity), the action determination engine 168 can decide not to change the setting of the lights and not to change the setting of the camera. The setting of the lights can include the brightness of the light and/or the color of the light.

For example, the first criteria can include that the measurement of the turbidity is larger than a first threshold (e.g., 100 NTU) and smaller than a second threshold (e.g., 1000 NTU). If the measurement of the turbidity is larger than the first threshold and smaller than the second threshold, this can indicate that the water (e.g., the water 114) has medium turbidity. The action determination engine 168 can determine to decrease the lighting such that there is less reflection from the particles in order to capture better observation data of the water. The lights can belong to the camera subsystem 102 (e.g., being a part of the camera), or can be an independent light source that is not a part of the camera subsystem 102. As another example, the action determination engine 168 can determine to change the color of the light, e.g., changing from a blue light to a red light.

In some implementations, the action determination engine 168 can obtain second criteria associated with the measurement of the turbidity, and can determine that the measurement satisfies the second criteria. In response to determining that the measurement satisfies the second criteria, the action determination engine 168 can change the position of a camera in the camera subsystem 102. In response to determining that the measurement does not satisfy the second criteria, the action determination engine 168 can decide not to change the position of a camera in the camera subsystem 102.

For example, the second criteria can include that the measurement of the turbidity is larger than a threshold (e.g., 100 NTU). If the measurement of the turbidity is larger than the threshold, this can indicate that the particular portion or layer of water has high turbidity. Because the particular portion or layer of water (e.g., the first region 124 of water) is opaque due to high turbidity, changing the lights may not be effective with regard to capturing better observation data of the water. The action determination engine 168 can determine to change a position of the camera to another portion or another layer of the water (e.g., the second region 123 of water) where the measurement of the turbidity is lower.

A first example scenario of turbidity determination works as follows.

In stage (A), the camera subsystem 102 provides image data 155 to the perception engine 160. The image data 155 can include one or more images or one or more videos of the water 104. As shown in FIG. 1, the water 104 is clear and has low turbidity. The perception engine 160 can detect a plurality of blobs in the image data 155 using a blob detector. Because the water 104 has low turbidity, the perception engine 160 may only detect a small amount of blobs (e.g., a number that is less than a threshold, such as thirty in an image. The perception engine 160 can determine a distribution of the plurality of blobs. For example, because the water 104 has low turbidity, the distribution of the plurality of blobs can include an even distribution of blobs of small sizes (e.g., a size that is smaller than 0.5 mm), medium sizes (e.g., a size that is between 0.5 mm and 5 mm), and large sizes (e.g., a size that is larger than 5 mm). The perception engine 160 can generate a histogram of the sizes of the blobs.

In stage (B), the perception engine 160 can provide the histogram of the sizes of the blobs to a turbidity prediction engine 166. The turbidity prediction engine 166 can determine, from the distribution of the plurality of blobs, a measurement associated with the turbidity of the water, e.g., using a trained machine learning model. For example, based on the histogram of the sizes of the blobs, the turbidity prediction engine 166 can generate a turbidity score in NTU, e.g., 0.1 NTU.

In stage (C), the perception engine 160 can provide a signal associated with the turbidity measurement. The signal can include the turbidity score in NTU, or a level of turbidity (e.g., low, medium, high). For example, the perception engine 160 can send a signal indicating "low turbidity" to an action determination engine 168.

In stage (D), after receiving the signal, the action determination engine 168 can determine an action or non-action based on the signal. For example, after receiving the signal indicating that the water 104 has low turbidity, the action determination engine 168 can determine that there is no change 109 to the setting of the camera. Because the water 104 is clear and has low turbidity, the camera can capture high quality images. So there is no need to change the lights or change the position of the camera.

A second example scenario of turbidity determination works as follows.

In stage (E), the camera subsystem 102 provides image data 155 to the perception engine 160. The image data 155 can capture an image of the water 114 indicating that the water 114 is unclear and has medium turbidity. The perception engine 160 can detect a plurality of blobs in the image data 155 using a blob detector, and can determine a distribution of the plurality of blobs. For example, the perception engine 160 can generate a histogram of the sizes of the blobs. Because the water 114 has medium turbidity, the distribution of the plurality of blobs can include a large amount of small blobs (e.g., 80% of the detected blobs) and a small amount of medium to large blobs (e.g., 20% of the detected blobs).

In stage (F), the perception engine 160 can provide the histogram of the sizes of the blobs to a turbidity prediction engine 166. Based on the histogram of the sizes of the blobs, the turbidity prediction engine 166 can generate, e.g., using a trained machine learning model, a measurement associated with the turbidity of the water, e.g., a turbidity score of 500 NTU.

In stage (G), the perception engine 160 can send a signal indicating "medium turbidity" to an action determination engine 168. In stage (H), the action determination engine 168 can determine to decrease the lighting 119 of the camera 102. The particles suspended in the water can generate too much reflection of lights, thus making the camera subsystem 102 difficult to capture high quality image data. By decreasing the lighting (e.g., an independent light source, or lights integrated in the camera), the camera subsystem 102 can capture image data with improved image quality. In some implementations, the action determination engine 168 may determine to increase the lighting of the camera in response to receiving a signal indicating "medium turbidity".

A third example scenario of turbidity determination works as follows.

In stage (I), the camera subsystem 102 provides image data 155 to the perception engine 160. The image data 155 can capture an image of a first region 124 of the water indicating that the first region 124 of the water is opaque and has high turbidity. The perception engine 160 can detect a plurality of blobs in the image data 155 using a blob detector, and can determine a distribution of the plurality of blobs. For example, the perception engine 160 can generate a histogram of the sizes of the blobs. Because the first region 124 of the water has high turbidity, the distribution of the plurality of blobs can include a significant amount of small blobs (e.g., 99% of detected blobs).

In stage (J), the perception engine 160 can provide the histogram of the sizes of the blobs to a turbidity prediction engine 166. Based on the histogram of the sizes of the blobs, the turbidity prediction engine 166 can generate, e.g., using a trained machine learning model, a measurement associated with the turbidity of the water, e.g., a turbidity score of 2000 NTU.

In stage (K), the perception engine 160 can send a signal indicating "high turbidity" to an action determination engine 168. In stage (L), the action determination engine 168 can determine to change the position 129 of the camera. The particles suspended in the water can generate too much reflection of lights, thus making the camera subsystem 102 impossible to capture high quality image data. The action determination engine 168 can determine to move the position of the camera from a first region 124 of the water to a second region 123 of the water, e.g., lowering the camera through the winch subsystem 108. The second region 123 of the water can have lower turbidity than the first region 124 of the water. Therefore, the camera subsystem 102 can capture image data with improved image quality.

Figure 2:
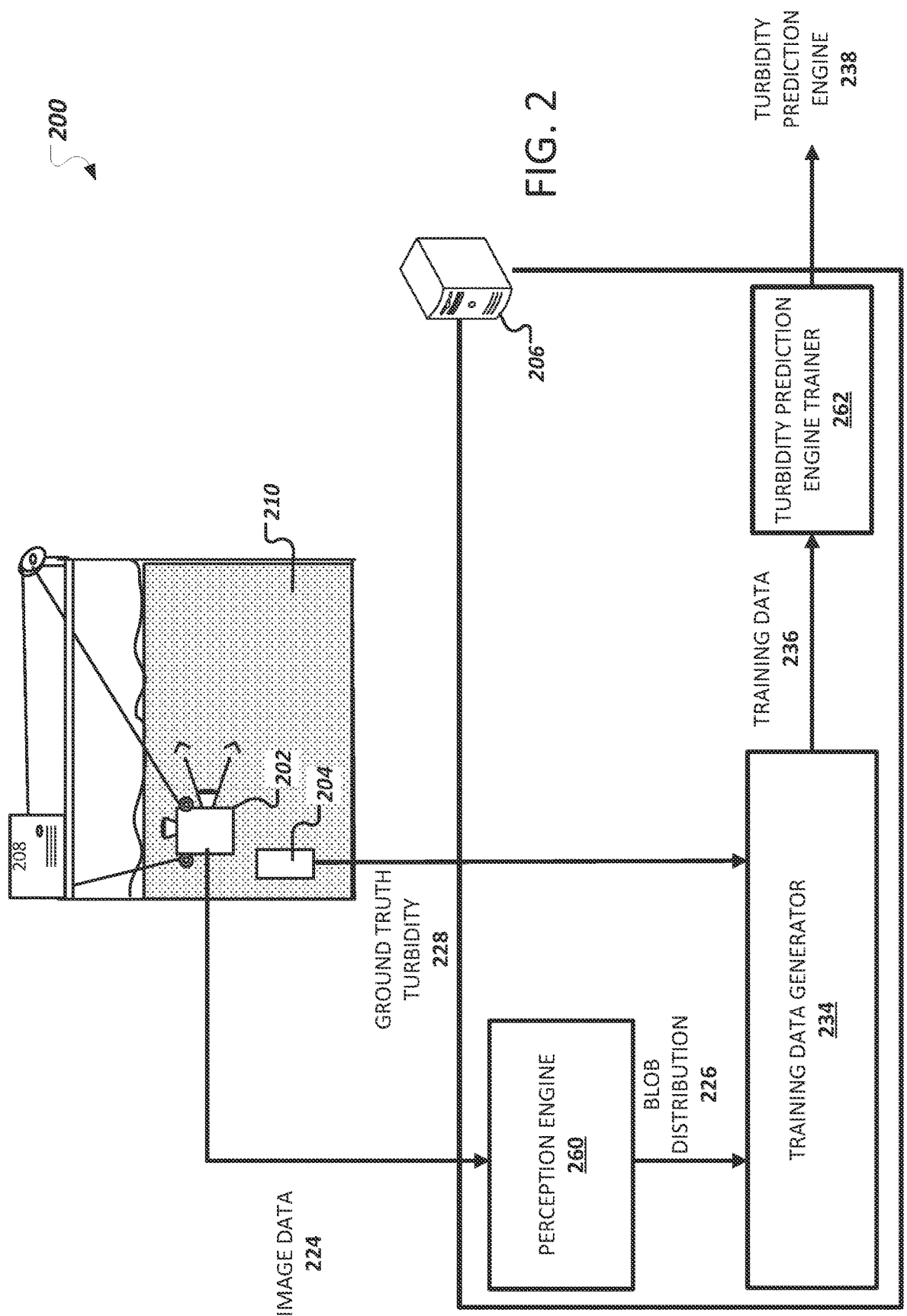
FIG. 2 is a diagram illustrating an example system for training a turbidity prediction engine.

FIG. 2 is a diagram illustrating an example system 200 for training a turbidity prediction engine. The system 200 can include one or more camera subsystems 202 each containing one or more cameras. The system 200 can include a turbidity sensor 204 that can generate a ground truth turbidity 228. The system 200 can include a perception engine 260, a training data generator 234, and a turbidity prediction engine trainer 262. The perception engine 260, the training data generator 234, and the turbidity prediction engine trainer 262 can be implemented in one or more computing devices 206 (e.g., computers or servers). The one or more computing devices 206 can be at a location that is away from the water 210 and the one or more camera subsystems 202.

The camera subsystem 202 can include one or more image capture devices that capture image data 224. The image data 224 can include one or more images or one or more videos. The image data 224 can depict an environment of the water 210 that may or may not include aquatic livestock. The camera subsystem 202 can be similar to the camera subsystem 102 described above in connection with FIG. 1.

The perception engine 260 can receive the image data 224 and apply computer vision models to generate a blob distribution 226. For example, the perception engine 260 can detect, using a blob detector, a plurality of blobs in the image data 224 and the blobs can represent particles suspended in the water 210. The blob distribution 226 can include a histogram of the sizes of the blobs. The process of generating a blob distribution 226 can be similar to the process of generating a blob distribution (e.g., a histogram) described above in connection with FIG. 1. The perception engine 260 can send the blob distribution to the training data generator 234. The blob distribution 226 can be a part of the training data 236 that can be used by the turbidity prediction engine trainer 262 to train the turbidity prediction engine 238.

A turbidity sensor 204 can be placed in the water 210 near the one or more cameras of the camera subsystem 202. The turbidity sensor 204 can measure the amount of light that is scattered by the suspended particles in water 210. The turbidity sensor 204 can include a nephelometer that measures the turbidity using a light source. The light source of the turbidity sensor can include an infrared emitting diode or a tungsten-filament lamp. The turbidity sensor 204 can generate a ground truth turbidity 228. The ground truth turbidity can be measured in NTU. For example, the turbidity sensor 204 can generate a ground truth turbidity 228 of the water 210, e.g., a measurement of turbidity of 300 NTU. The turbidity sensor 204 can send the ground truth turbidity 228 to the training data generator 234.

The training data generator 234 receives the blob distribution 226 and a corresponding ground truth turbidity 228. The training data generator 234 generates training data 236 that includes a plurality of training examples and each training example can include a blob distribution 226 and a corresponding ground truth turbidity 228. For example, the training data 236 can include 1000 training examples, and each training example includes a histogram of the sizes of the blobs detected in water and a ground truth turbidity score of the same water. The training data generator 234 sends the training data 236 to a turbidity prediction engine trainer 262.

The turbidity prediction engine trainer 262 can use the training data 236 to train a turbidity prediction engine 238 (e.g., the turbidity prediction engine 166 in the system 100 of FIG. 1). The turbidity prediction engine 238 can include a machine learning model (e.g., a regression model, a deep neural network, etc.) that can generate a measurement associated with the turbidity of the water from an input that includes a blob distribution. The turbidity prediction engine 238 can include a plurality of parameters. The turbidity prediction engine trainer 262 can perform the training at one or more computing devices 206 that can train a machine learning model.

During training, the turbidity prediction engine trainer 262 can generate updates of the plurality of parameters of the machine learning model using the training data 236. For each training example in the training data, the trainer 262 can generate, from the blob distribution 226 of the training example, a predicted measurement of the turbidity using current values of the plurality of parameters. The trainer 262 can calculate a loss by comparing the predicted measurement of the turbidity with the ground truth turbidity 228 of the training example. For example, the loss can be a mean-squared loss or an L1 loss. The trainer 262 can update the values of the plurality of parameters of the machine learning model based on the loss. The trainer 262 can train the machine learning model in multiple iterations.

The trainer 262 can determine that the training is completed and can generate final values of the parameters of the machine learning model. In some implementations, the trainer 262 can determine that the training is completed when a predetermined number of iterations of training has been completed. In some implementations, the trainer 262 can determine that the training is completed when the loss is less than a predetermined threshold or when the updates to the plurality of parameters are less than one or more predetermined thresholds. After the training is completed, the trainer 262 can generate a trained turbidity prediction engine 238 with the final values of the plurality of parameters of the machine learning model. The trainer 262 can provide the trained turbidity prediction engine 238 to a system for determining turbidity in an aquaculture environment (e.g., the system 100 in FIG. 1).

Figure 3:
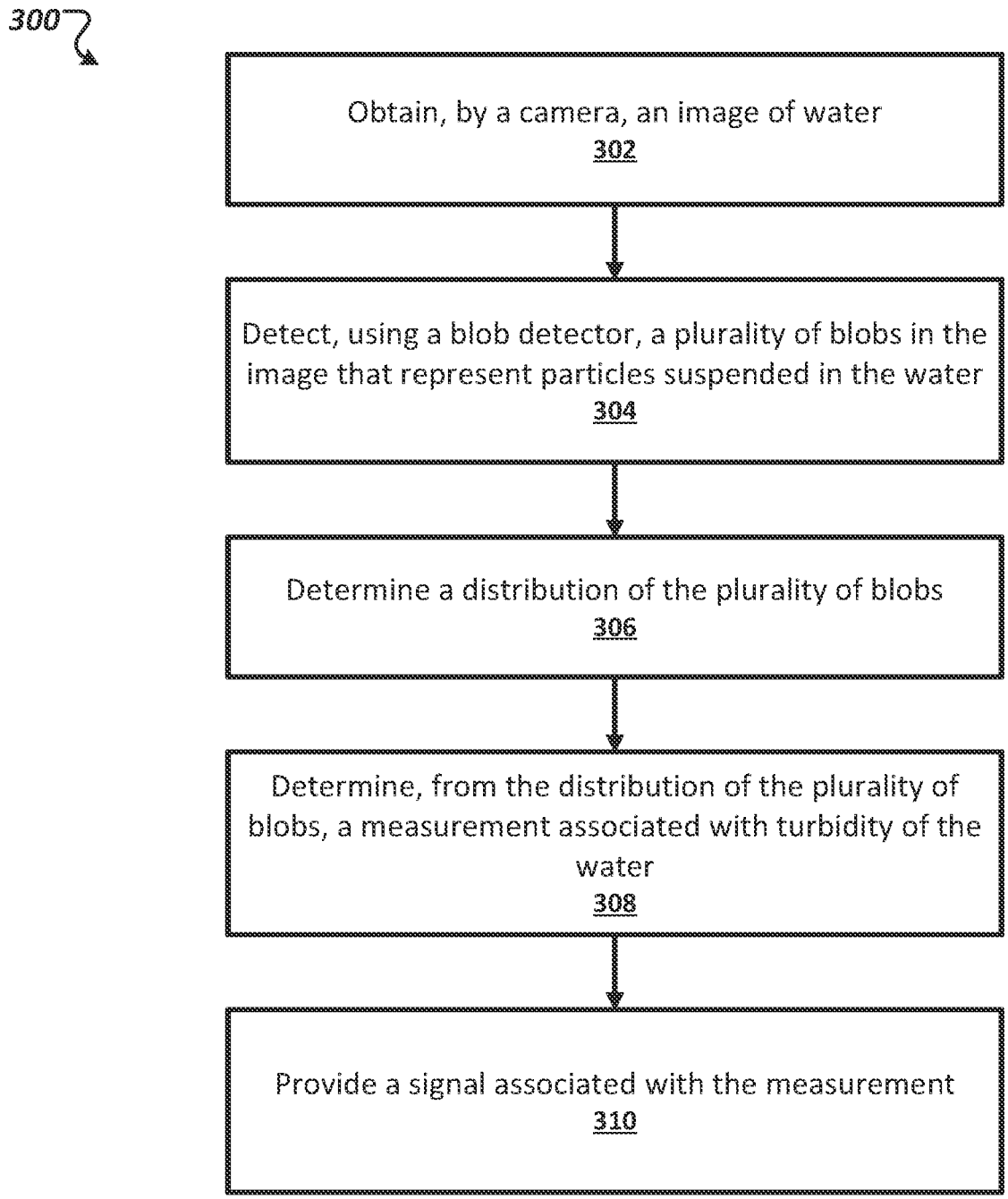
FIG. 3 is a flow chart illustrating an example of a process for turbidity determination.

FIG. 3 is a flow chart illustrating an example of a process 300 for turbidity determination. The process 300 can be performed by one or more computer systems, for example, the one or more camera subsystems 102, the one or more computing devices 101, the perception engine 160, the turbidity prediction engine 166, the action determination engine 168, or a combination of these. In some implementations, some or all of the process 300 can be performed by the system 100, or by another computer system located near the water 104 or at a remote location.

The system obtains, by a camera, an image of water (302). For example, a camera of a camera subsystem 102 can capture image data 155 of the water 104. The image data 155 can depict an optical property of the aquatic environment of the water 104. The water 104 may or may not contain livestock, such as fish.

The system detects, using a blob detector, a plurality of blobs in the image that represent particles suspended in the water (304). For example, a perception engine 160 can receive the image data 155 from the camera subsystem 102. The perception engine can include computer vision models and algorithms that process the image data 155. The perception engine 160 can include a blob detector that detects a continuous area that is enclosed and has a certain brightness level and a certain size. The perception engine 160 can use the blob detector to detect a plurality of blobs in the image. The plurality of blobs can represent particles suspended in the water. The amount and sizes of particles suspended in the water can cause different levels of turbidity of the water.

The system determines a distribution of the plurality of blobs (306). In some implementations, the system can determine sizes of the plurality of blobs. The system can generate a histogram of the sizes of the plurality of blobs. For example, the perception engine 160 can measure sizes of the blobs, e.g., measured in millimeters. Large blob (e.g., a size that is larger than 5 mm) can block a large area of view of the camera, while a large amount of small blobs (e.g., a size that is smaller than 0.5 mm) can cause a high level of turbidity due to reflections of light caused by the blobs. The perception engine 160 can generate a histogram of the sizes of the blobs by grouping the sizes of the blobs into different ranges (e.g., user-specified ranges).

The system determines, from the distribution of the plurality of blobs, a measurement associated with turbidity of the water (308). In some implementations, the measurement associated with the turbidity of the water can represent Nephelometric Turbidity Units (NTU). For example, the measurement associated with the turbidity of the water can be a number that is within a range of 0.1 NTU to 3000 NTU.

In some implementations, the system can provide the histogram of the sizes of the plurality of blobs as an input to a machine learning model. The system can generate the measurement associated with the turbidity of the water using the machine learning model. For example, the machine learning model can include a regression model that can generate a predicted measurement of the turbidity of the water from the histogram of the sizes of the blobs. The predicted measurement of the turbidity can be a turbidity score in NTU.

In some implementations, the machine learning model can be trained with training data including images previously captured by the camera and respective ground truth measurement measured by a turbidity sensor. For example, referring to FIG. 2, a turbidity sensor 204 can be placed in the water and can be placed close to a camera of the camera subsystem 202. Thus, the turbidity sensor can generate a measurement of turbidity of the same water as the water that is captured by the camera. The turbidity sensor 202 can generate a ground truth turbidity 228. A training data generator can receive: (i) blob distribution 226 of the image data 224 of the water 210 captured by the camera subsystem 202, and (ii) the ground truth turbidity 228 of the water 210 measured by the turbidity sensor 204. The training data generator 234 can generate training data 236 that includes a plurality of training examples, and each training example can include a blob distribution 226 and its corresponding ground truth turbidity 228. A turbidity prediction engine trainer 262 can train a turbidity prediction engine 238 (e.g., the machine learning model of the turbidity prediction engine 238) using the training data 236.

In some implementations, the system can detect a particular object (e.g., a fish or a net) in the image using an object detector. The object detector uses computer vision and image processing techniques to detect instances of semantic objects of a certain class in images and videos. Examples of object detectors based on a neural network include Fast R-CNN (Girshick, Ross. *"Fast r-cnn."* *Proceedings of the IEEE international conference on computer vision.* 2015), Faster R-CNN (Ren, Shaoqing, et al. *"Faster r-cnn: Towards real-time object detection with region proposal networks."* *Advances in neural information processing systems* 28 (2015): 91-99), Single Shot MultiBox Detector (SSD) (Liu, Wei (October 2016). *"SSD: Single shot multibox detector"*. *Computer Vision—ECCV 2016. European Conference on Computer Vision. Lecture Notes in Computer Science.* 9905. pp. 21-3), You Only Look Once (YOLO) (Redmon, Joseph (2016). *"You only look once: Unified, real-time object detection"*. *Proceedings of the IEEE Conference on Computer Vision and Pattern Recognition*). Some object detectors can be based on features, such as Harr features, Scale-Invariant Feature Transform (SIFT) features, Histogram of Oriented Gradients (HOG) features. The object detector is different from the blob detector because the object detector can detect semantic objects in the water (e.g., a fish or a net), while the blob detector can detect particles suspended in the water that has a circular shape.

The system can determine that a subset of the plurality of blobs detected in the image overlaps with the particular object. The system can determine the distribution of the plurality of blobs to not represent the subset of the plurality of blobs. For example, the perception engine 260 can detect a fish or a net in the image data 155. Because one or more portions of a fish or a net may have bright reflections of light, the particular object (e.g., the fish or the net) can be detected as one or more blobs by the blob detector. For example, an eye or a scale of a fish may have bright reflections of light, and the one or more portions of the fish or the net can be recognized as blobs by a blob detector. The system can determine that a subset of the plurality of blobs detected in the image overlaps with the fish or the net. The system can determine the distribution of the plurality of blobs to not represent the subset of the plurality of blobs. In some implementations, the blob detector can be configured or trained to not detect the blobs that correspond to a particular object detected in the image. Therefore, the distribution of the plurality of blobs can represent the distribution of the blobs that correspond to the particles suspended in water, rather than the blobs that correspond to the bright spots from a fish or a net.

The system provides a signal associated with the measurement (310). The signal can contain one or more metrics, such as a metric associated with turbidity, a quantized metric of turbidity (such as "high", "medium" and "low"), a metric associated with the change in turbidity, a metric associated with the rate of change of turbidity, etc. For example, the signal can include a turbidity score in NTU. As another example, the signal can include a level of turbidity, e.g., "low turbidity", "medium turbidity", and "high turbidity".

In some implementations, the system can obtain first criteria associated with the measurement. The system can determine that the measurement satisfies the first criteria, and in response, the system can change a setting of lights. For example, the system can change the brightness of the lights, including decreasing the lighting. As another example, the system can change the color of the lights, such as using a red light instead of a blue light, or using a blue light instead of using a red light. In some implementations, the system can provide the signal to trigger a change of a setting of the camera. For example, upon receiving a signal indicating "high turbidity", the system can increase the exposure time of the camera, or increase the light sensitivity of the camera.

In some implementations, the system can obtain second criteria associated with the measurement. The system can determine that the measurement satisfies the second criteria, and in response, the system can change the position of the camera. For example, the system can determine that the first region 124 of water where the camera 102 is located has high turbidity and the system cannot get a good image of the aquatic livestock in the water. The system can move the camera 102 out of the first region 124 of water and move to the second region 123 of the water that has lower turbidity. Then the camera may be able to capture an image with improved image quality.

In some implementations, the system can obtain third criteria associated with the measurement. The system can determine that the measurement satisfies the third criteria, and in response, the system can change the setting of a feeding subsystem. For example, the system can determine that the region 124 of the water has medium to high turbidity. Because fish can eat less aggressively when they cannot see the feed, the system can decrease the feeding amount. For example, the feeding subsystem can reduce the quantity of feed released or the rate at which it is released.

In some implementations, the system (e.g., the action determination engine 168) can include a machined learning model and the machine learning model can process the signal associated with the measurement of the turbidity as input and produce one or more scores associated with a plurality of recommended actions. For example, the action determination engine 168 can generate a likelihood for each of the recommended actions (e.g., 40% no change 109, 50% decreasing the lighting 119 of the camera 102, and 10% changing the position 109 of the camera 102). The action determination engine 168 or a user can determine one or more actions based on the one or more scores associated with the plurality of recommended actions.

In some implementations, the system can provide one or more recommended action signals associated with the evaluation of the turbidity signal to one or more aquaculture management subsystems, such as a feeder subsystem and a rig navigation subsystem. The signal can be provided over a network, such as the internet or a private network, using conventional communication protocols over a wired or wireless connection.

While this specification has largely focused on turbidity determined using data produced by a perception system associated with a blob detector, additional implementations are possible. For example, in some implementations, the computer vision data used for biomass estimation can be intercepted and reused to determine distance distributions of the livestock, and the distance distributions can be used as additional factors to determine turbidity levels. Multiple abrupt changes to the turbidity level in the water can indicate faults within one or more components of an environmental management system and can trigger an alert to a maintenance subsystem. Such an alert can also be used to add a marker to the images produced, indicating potential inaccuracies in the captured data.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method, comprising:
   obtaining, by a camera, an image of water in a fish enclosure;
   detecting, using a blob detector, a plurality of blobs in the image that represent particles suspended in the water in the fish enclosure;

determining a respective size associated with each of the plurality of blobs that represent the particles suspended in the water in the fish enclosure;

generating a histogram that, for each of a plurality of size intervals, includes a count of blobs in the fish enclosure whose size is in the size interval;

providing the histogram of the counts of blobs in the fish enclosure for each of the plurality of size intervals as an input to a machine learning model, the machine learning model having been trained to output values representing estimate amounts of turbidity in fish enclosures using training data that includes (i) histograms generated from images that were previously captured by cameras in the fish enclosures, and (ii) ground truth values that were measured by turbidity sensors in the fish enclosures are not cameras;

in response to providing the histogram as the input to the machine learning model, receiving, from the machine learning model, a value representing an estimated amount of turbidity of the water in the fish enclosure; and when the value does not satisfy water clarity criteria, providing a signal to an image processor to discard or halt processing of images.

2. The computer-implemented method of claim 1, wherein the value representing the estimated amount of the turbidity of the water represents a quantity of Nephelometric Turbidity Units (NTU).

3. The computer-implemented method of claim 1, comprising:

providing a signal to change a setting of lights that are associated with the camera in the fish enclosure.

4. The computer-implemented method of claim 1, comprising providing a signal to change a position of the camera in the fish enclosure.

5. The computer-implemented method of claim 1, comprising determining a distribution of the plurality of blobs, comprising:

detecting a particular object in the image using an object detector that is different than the blob detector;

determining that a subset of the plurality of blobs detected in the image overlaps with the particular object; and determining the distribution of the plurality of blobs to not represent the subset of the plurality of blobs.

6. The computer-implemented method of claim 1, comprising providing a signal to change a setting of the camera.

7. The computer-implemented method of claim 1, comprising:

providing a signal to change a setting of a feeding subsystem.

8. The method of claim 1, wherein the signal classifies the fish enclosure as having a first level of turbidity, a second level of turbidity, or a third level of turbidity.

9. A system comprising:

one or more computers and one or more storage devices storing instructions that are operable, when executed by the one or more computers, to cause the one or more computers to perform operations comprising:

obtaining, by a camera, an image of water in a fish enclosure;

detecting, using a blob detector, a plurality of blobs in the image that represent particles suspended in the water in the fish enclosure;

determining a respective size associated with each of the plurality of blobs that represent the particles suspended in the water in the fish enclosure;

generating a histogram that, for each of a plurality of size intervals, includes a count of blobs in the fish enclosure whose size is in the size interval;

providing the histogram of the counts of blobs in the fish enclosure for each of the plurality of size intervals as an input to a machine learning model, the machine learning model having been trained to output values representing estimate amounts of turbidity in fish enclosures using training data that includes (i) histograms generated from images that were previously captured by cameras in the fish enclosures, and (ii) ground truth values that were measured by turbidity sensors in the fish enclosures are not cameras;

in response to providing the histogram as the input to the machine learning model, receiving, from the machine learning model, a value representing an estimated amount of turbidity of the water in the fish enclosure; and when the value does not satisfy water clarity criteria, providing a signal to an image processor to discard or halt processing of images.

10. The system of claim 9, wherein the value representing the estimated amount of the turbidity of the water represents a quantity of Nephelometric Turbidity Units (NTU).

11. The system of claim 9, wherein the operations comprise:

providing a signal to change a setting of lights that are associated with the camera in the fish enclosure.

12. The system of claim 9, wherein the operations comprise providing a signal to change a position of the camera in the fish enclosure.

13. The system of claim 9, the operations comprise determining a distribution of the plurality of blobs, comprising:

detecting a particular object in the image using an object detector that is different than the blob detector;

determining that a subset of the plurality of blobs detected in the image overlaps with the particular object; and determining the distribution of the plurality of blobs to not represent the subset of the plurality of blobs.

14. The system of claim 9, wherein the operations comprise providing a signal to change a setting of the camera.

15. The system of claim 9, wherein the operations comprise:

providing a signal to change a setting of a feeding subsystem.

16. A non-transitory computer-readable medium storing software comprising instructions executable by one or more computers which, upon such execution, cause the one or more computers to perform operations comprising:

obtaining, by a camera, an image of water in a fish enclosure;

detecting, using a blob detector, a plurality of blobs in the image that represent particles suspended in the water in the fish enclosure;

determining a respective size associated with each of the plurality of blobs that represent the particles suspended in the water in the fish enclosure;

generating a histogram that, for each of a plurality of size intervals, includes a count of blobs in the fish enclosure whose size is in the size interval;

providing the histogram of the counts of blobs in the fish enclosure for each of the plurality of size intervals as an input to a machine learning model, the machine learning model having been trained to output values representing estimate amounts of turbidity in fish enclosures using training data that includes (i) histograms generated from images that were previously captured by cameras in the fish enclosures, and (ii) ground truth values that were measured by turbidity sensors in the fish enclosures are not cameras;

in response to providing the histogram as the input to the machine learning model, receiving, from the machine learning model, a value representing an estimated amount of turbidity of the water in the fish enclosure; and when the value does not satisfy water clarity criteria, providing a signal to an image processor to discard or halt processing of images.

17. The medium of claim 16, wherein the value representing the estimated amount of the turbidity of the water represents a quantity of Nephelometric Turbidity Units (NTU).

18. The medium of claim 16, wherein the operations comprise:

providing a signal to change a setting of lights that are associated with the camera in the fish enclosure.

19. The medium of claim 16, wherein the operations comprise:

providing a signal to change a position of the camera in the fish enclosure.

20. The medium of claim 16, the operations comprise determining a distribution of the plurality of blobs, comprising:

detecting a particular object in the image using an object detector that is different than the blob detector;

determining that a subset of the plurality of blobs detected in the image overlaps with the particular object; and determining the distribution of the plurality of blobs to not represent the subset of the plurality of blobs.

21. The medium of claim 16, wherein the operations comprise providing a signal to change a setting of the camera.

22. The medium of claim 16, wherein the operations comprise:

providing a signal to change a setting of a feeding subsystem.

23. The medium of claim 16, wherein the signal classifies the fish enclosure as having a first level of turbidity, a second level of turbidity, or a third level of turbidity.

* * * * *